(12) United States Patent
Dyballa et al.

(10) Patent No.: US 9,217,003 B2
(45) Date of Patent: Dec. 22, 2015

(54) PREPARATION OF 6,6'-((3,3'-DI-TERT-BUTYL-5,5'-DIMETHOXY-[1,1'-BIPHENYL]-2,2'-DIYL)BIS(OXY))BIS(2,4,8,10-TETRA-METHYLDIBENZO[D,F][1,3,2]DIOXA-PHOSPHEPINE)

(71) Applicants: Katrin Marie Dyballa, Recklinghausen (DE); Robert Franke, Marl (DE)

(72) Inventors: Katrin Marie Dyballa, Recklinghausen (DE); Robert Franke, Marl (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/618,361

(22) Filed: Feb. 10, 2015

(65) Prior Publication Data

US 2015/0225435 A1    Aug. 13, 2015

(30) Foreign Application Priority Data

Feb. 12, 2014 (DE) .......................... 10 2014 202 499

(51) Int. Cl.
*C08K 5/527* (2006.01)
*C07F 9/6574* (2006.01)

(52) U.S. Cl.
CPC ......... *C07F 9/65746* (2013.01); *C07F 9/65744* (2013.01)

(58) Field of Classification Search
CPC ...................................................... C08K 5/527
See application file for complete search history.

(56) References Cited

U.S. PATENT DOCUMENTS

| 4,769,498 A | 9/1988 | Billig et al. |
| 5,723,641 A | 3/1998 | Tam et al. |

FOREIGN PATENT DOCUMENTS

| CN | 101684130 B | 5/2013 |
| DE | 102013219506 | * 4/2014 |

* cited by examiner

*Primary Examiner* — Sun Jae Yoo
(74) *Attorney, Agent, or Firm* — Oblon, McClelland, Maier & Neustadt, L.L.P.

(57) ABSTRACT

A process for preparing 6,6'-((3,3'-di-tert-butyl-5,5'-dimethoxy-[1,1'-biphenyl]-2,2'-diyl)bis(oxy))bis(2,4,8,10-tetramethyldibenzo[d,f][1,3,2]dioxaphosphepine) is provided.

7 Claims, No Drawings

PREPARATION OF 6,6'-((3,3'-DI-TERT-BUTYL-5,5'-DIMETHOXY-[1,1'-BIPHENYL]-2,2'-DIYL)BIS(OXY))BIS(2,4,8,10-TETRAMETHYL-DIBENZO[D,F][1,3,2]DIOXAPHOSPHEPINE)

CROSS REFERENCE TO RELATED APPLICATIONS

This application claims priority to German Application No. 102014202499.4 filed Feb. 12, 2014, the disclosure of which is incorporated herein by reference in its entirety.

BACKGROUND OF THE INVENTION

The invention relates to a process for preparing 6,6'-((3,3'-di-tert-butyl-5,5'-dimethoxy-[1,1'-biphenyl]-2,2'-diyl)bis(oxy))bis(2,4,8,10-tetramethyldibenzo[d,f][1,3,2]dioxaphosphepine).

Phosphorus-containing compounds, as ligands, play a crucial role in a multitude of reactions. Said compounds include phosphite ligands, i.e., compounds comprising P—O bonds, used in hydrogenation, hydrocyanation and especially hydroformylation.

The reactions between olefin compounds, carbon monoxide and hydrogen in the presence of a catalyst to give the aldehydes comprising one additional carbon atom are known as hydroformylation or oxo synthesis. These reactions often employ compounds of the group VIII transition metals as catalyst. Known ligands include, for example, compounds of the phosphine, phosphite and phosphonite classes each comprising trivalent phosphorus $P^{III}$. A good overview of the state of the art in the field of olefin hydroformylation may be found in B. CORNILS, W. A. HERRMANN, "Applied Homogeneous Catalysis with Organometallic Compounds", vol. 1 & 2, VCH, Weinheim, N.Y., 1996 or R. Franke, D. Selent, A. Börner, "Applied Hydroformylation", Chem. Rev., 2012, DOI:10.1021/cr3001803.

The synthesis of symmetric bisphosphites is conventionally known as described in U.S. Pat. No. 4,769,498 for example, and the use thereof in catalytically active transition metal-containing compositions for the hydroformylation of unsaturated compounds.

U.S. Pat. No. 4,769,498 and also U.S. Pat. No. 5,723,641 describe the preparation of preferably symmetric bisphosphites and the use thereof as ligands for hydroformylation. The symmetric bisphosphite ligands used in the hydroformylation are prepared at low temperatures. Adherence to these low temperatures is absolutely necessary since according to the description of these documents higher temperatures would lead to unwanted rearrangements and ultimately to asymmetric bisphosphites.

When symmetric bisphosphites are employed as ligands in transition metal-catalysed hydroformylation they generally exhibit distinctly higher reactivities and improved n-regioselectivity (see Rhodium-catalyzed Hydroformylation, ed. by P. W. N. M. van Leeuwen and C. Claver, Kluwer Academic Publishers 2006, AA Dordrecht, NL, pages 45-46).

Synthetic routes to symmetric ligands are conventionally known. However, said routes generally give mixtures of symmetric and asymmetric ligands. Small quantities of these mixtures are separable using appropriate column chromatography processes for example. However, these separation processes are impracticable for larger quantities of product or for use on a large industrial scale.

Direct preparation of pure 6,6'-((3,3'-di-tert-butyl-5,5'-dimethoxy-[1,1'-biphenyl]-2,2'-diyl)bis(oxy))bis(2,4,8,10-tetramethyldibenzo[d,f][1,3,2]dioxaphosphepine) (I) has hitherto been unsuccessful since transesterification to generate asymmetric 4,8-di-tert-butyl-2,10-dimethoxy-6-((3,3',5,5'-tetramethyl-2'-(2,4,8,10-tetramethyldibenzo[d,f][1,3,2]dioxaphosphepin-6-yl)oxy)-[1,1'-biphenyl]-2-yl)oxy) dibenzo[d,f][1,3,2]dioxaphosphepine (II) takes place during the reaction.

It is an object of the present invention to provide a process whereby the compound 6,6'-((3,3'-di-tert-butyl-5,5'-dimethoxy-[1,1'-biphenyl]-2,2'-diyl)bis(oxy))bis(2,4,8,10-tetramethyldibenzo[d,f][1,3,2]dioxaphosphepine) (I) is obtained. Additionally, the proportion of 4,8-di-tert-butyl-2,10-dimethoxy-6-((3,3',5,5'-tetramethyl-2'-((2,4,8,10-tetramethyldibenzo[d,f][1,3,2]dioxaphosphepin-6-yl)oxy)-[1,1'-biphenyl]-2-yl)oxy)dibenzo[d,f][1,3,2]dioxaphosphepine (II) in the end product should also be very low.

It should preferably be possible to use the process on a large industrial scale. Processes unrealizable in large scale manufacture, such as separation by column chromatography for example, should therefore be eschewed.

SUMMARY OF THE INVENTION

This and other objects have been achieved according to the present invention, the first embodiment of which includes a process for preparing a compound of formula (I):

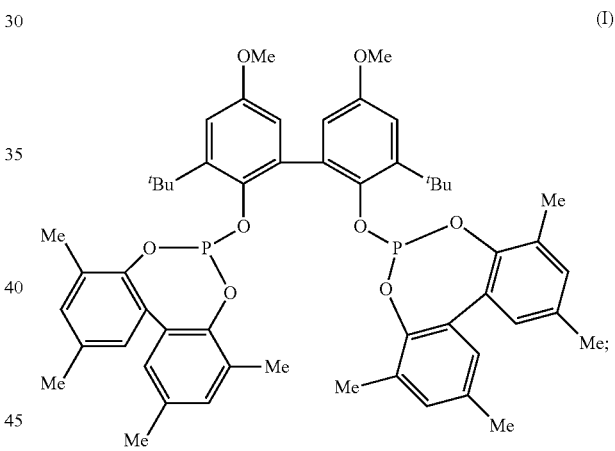

the process comprising:
a) reacting 3,3',5,5'-tetramethyl-2,2'-dihydroxybiphenyl with $PCl_3$ in an inert gas atmosphere to obtain a phosphorochloridite derivative;
b) reacting at least 2 equivalents of the phosphorochloridite derivative obtained in a) with 1 equivalent of 5,5'-dimethoxy-3,3'-di-tert-butyl-2,2'-dihydroxybiphenyl in an inert gas atmosphere to obtain a crude product;
c) adding to the crude product from b) a solvent or a solvent mixture comprising at least one solvent selected from the group consisting of: o-xylene, toluene, methanol, ethanol, butanol and isopropanol to obtain a crude product mixture;
d) heating the crude product mixture from c) to dissolve the crude product and obtain a solution;
e) cooling down the solution from d) to precipitate the compound according to formula (I) from the solution;
f) filtering-off the precipitated compound according to formula (I).

The foregoing paragraphs have been provided by way of general introduction, and are not intended to limit the scope of the following claims. The described embodiments, together with further advantages, will be best understood by reference to the following detailed description taken in conjunction with the accompanying drawings.

DETAILED DESCRIPTION OF THE PREFERRED EMBODIMENTS

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted. Where a numerical limit or range is stated, the endpoints are included. Also, all values and subranges within a numerical limit or range are specifically included as if explicitly written out.

In a first embodiment the present invention provides a process for preparing a compound according to formula (I):

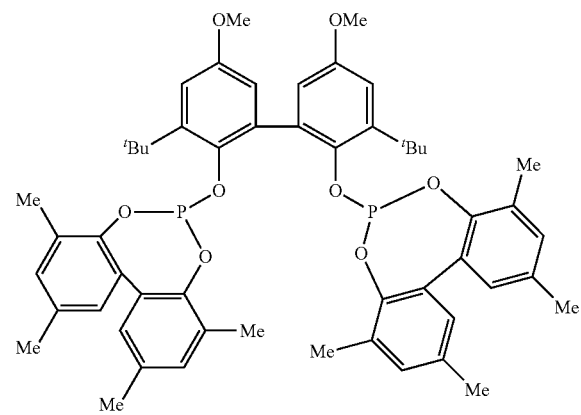

(I)

comprising:

a) reacting 3,3',5,5'-tetramethyl-2,2'-dihydroxybiphenyl with $PCl_3$ in an inert gas atmosphere to obtain a phosphorochloridite derivative;

b) reacting at least 2 equivalents of the phosphorochloridite derivative obtained in a) with 1 equivalent of 5,5'-dimethoxy-3,3'-di-tert-butyl-2,2'-dihydroxybiphenyl in an inert gas atmosphere to obtain a crude product;

c) adding to the crude product from b) a solvent or a solvent mixture comprising at least one solvent selected from the group consisting of: o-xylene, toluene, methanol, ethanol, butanol and isopropanol to obtain a crude product mixture;

d) heating the crude product mixture from c) to dissolve the crude product and obtain a solution;

e) cooling down the solution from d) to precipitate the compound according to formula (I) from the solution;

f) filtering-off the precipitated compound according to formula (I).

In one variant of the process, process operations c) to f) may be repeated.

In one variant of the process, the cooling down in e) may comprise cooling down to room temperature.

In one variant of the process, o-xylene may be used as solvent in c).

In one variant of the process, the mixture may be heated to a temperature in the range of from 80° C. to 140° C., preferably from 90° C. to 110° C. in d).

The mixture may be preferably stirred during heating.

In one variant of the process, the reacting in b) may be carried out in the presence of at least one base.

In one variant of the process, the base may be selected from: triethylamine ($NEt_3$), dimethylaminopyridine (DMAP), pyridine and tributylamine ($NBu_3$).

EXAMPLES

General Reaction Equation

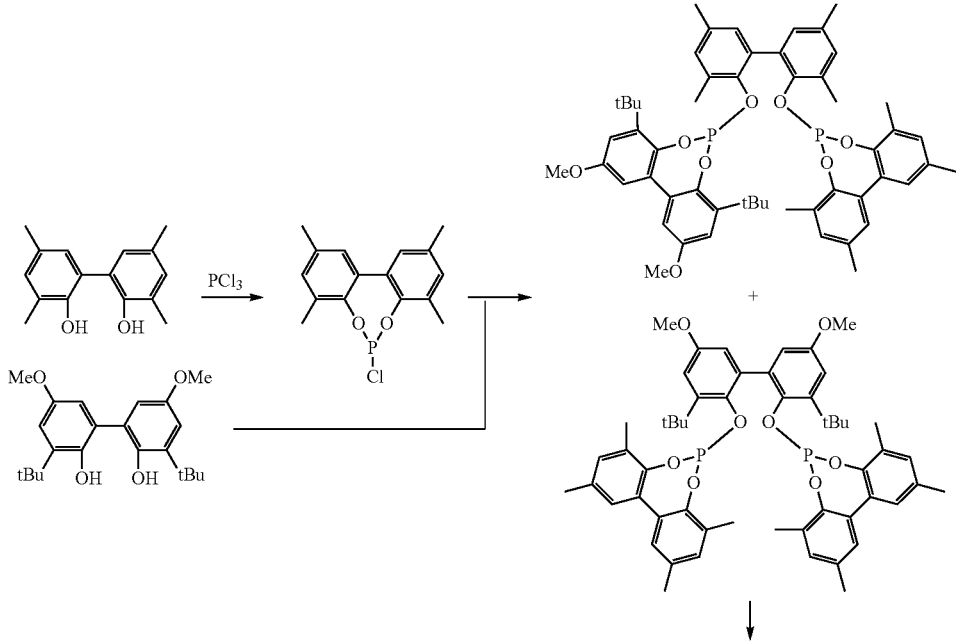

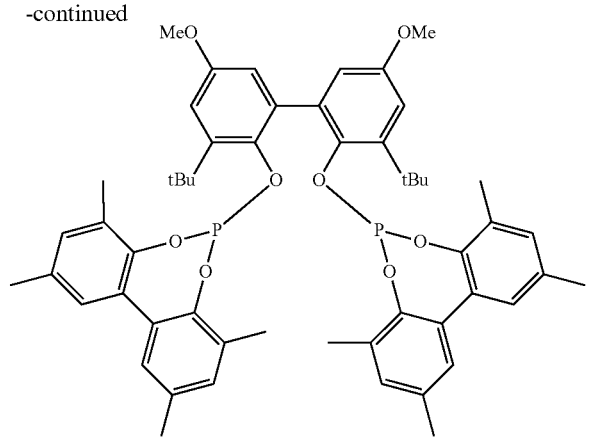

General Operating Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009). The product was characterized by NMR spectroscopy (Bruker Avance 500 MHz FT-NMR spectrometer). Chemical shifts are reported in ppm. The 31P NMR signals were referenced according to: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). The ratio of the two ligands to one another was determined by 31P NMR. The asymmetric ligand was characterized by two phosphorus signals while only one phosphorus signal was associated with the symmetric ligand.

Synthesis of 2,2'-bis(3,5-dimethylphenol)chlorophosphite

A secured 2 l Schlenk flask with magnetic stirrer was initially charged with 440 ml (692.56 g) of phosphorus trichloride. 120 g of 2,2'-bis(3,5-dimethylphenol) were weighed into a second secured 1 l Schlenk flask and 500 ml of dried toluene were added with stirring. The biphenol-toluene suspension was metered into the phosphorus trichloride over 4 h at 63° C. On completion of the addition, the reaction mixture was stirred overnight at temperature. The next morning, the solution was concentrated while warm (45° C.) and the product was obtained in 96.5% yield (153 g). $^{31}P$ NMR: 175.59 (94.8% 2,2'-bis(3,5-dimethylphenol)chlorophosphite), 4.4% various PCl compounds, 0.8% P—H compound.

Preparation of the Isomer Mixture from the Compounds (I) and (II):

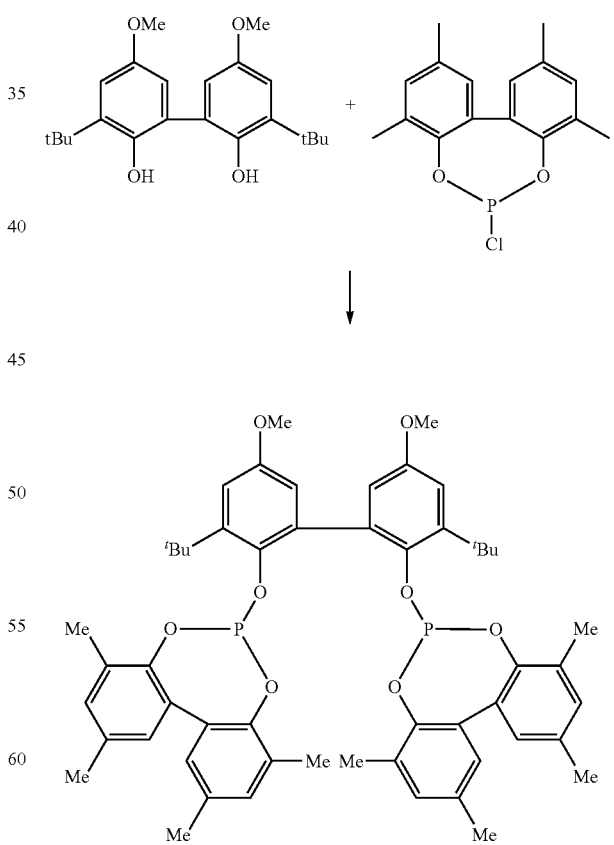

-continued

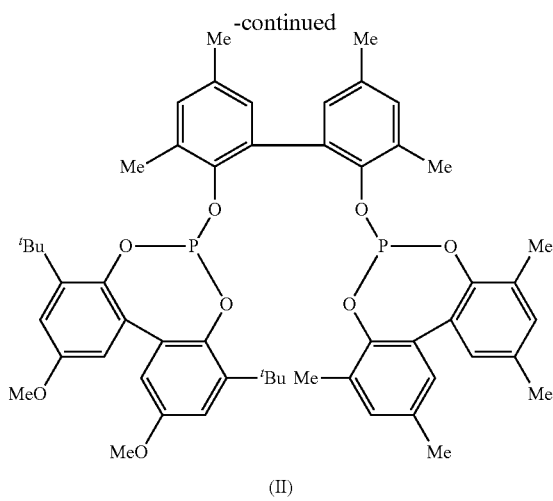

(II)

General Procedure:

In a 1000 ml Schlenk flask under protective gas, 38.75 g (0.121 mol) of 2,2'-bis(3,5-dimethylphenyl)chlorophosphite were dissolved in 150 ml of degassed acetonitrile (ACN) and heated to 45° C. In a second Schlenk flask (500 ml), 20.1 g (0.056 mol) of 3,3'-di-tert-butyl-5,5'-dimethoxy-[1,1'-biphenyl]-2,2'-diol were dissolved in 150 ml of degassed ACN and admixed with the respective base with stirring (the amount used is based on the chlorophosphite). The biphenol/base solution was then slowly added to the chlorophosphite solution in dropwise fashion. After a postreaction time of 1 h, the reaction solution was stirred overnight at 45° C. (Other temperatures or reaction times may be found in the tables.)

The solution was subsequently filtered and the solids were washed with 100 ml of warm (45° C.) ACN. The target product was obtained as a white solid (yield in %). $^{31}$P NMR (202.4 MHz, toluene-d$_8$): 142.5 and 140.9 (compound (II)), 139.2 (compound (I)).

TABLE 1

Variation of temperature (and base quantity)

| Temperature | Base equivalents | Base | Compound (II) [%] | Compound (I) [%] | Yield in [%] |
|---|---|---|---|---|---|
| 45° C. | 2.5 | DMAP | 46.6 | 53.4 | 51 |
| 0° C. | 2 | DMAP | 42.7 | 57.3 | 50 |
| 5° C. | 2 | DMAP | 47.8 | 52.2 | 89 |
| 45° C. | 2 | DMAP | 65.0 | 35.0 | 90 |

TABLE 2

Variation of base ratio

| Temperature | Bases | Ratio | Compound (II) [%] | Compound (I) [%] | Yield in [%] |
|---|---|---|---|---|---|
| 45° C. | pyr/NEt$_3$ | 4:1 | 78.2 | 21.8 | 56 |
| 45° C. | pyr/NEt$_3$ | 4:0.5 | 59.6 | 40.4 | 87 |
| 45° C. | pyr/NEt$_3$ | 4:0.25 | 59.7 | 40.3 | 80 |
| 45° C. | pyr/NEt$_3$ | 3:0.5 | 62.5 | 37.5 | 81 |
| 45° C. | pyr/NEt$_3$ | 2:0.5 | 69.0 | 31.0 | 84 |
| 45° C. | pyr/NBu$_3$ | 2:0.5 | 72.4 | 27.6 | 78 |

NBu$_3$: tributylamine
NEt$_3$: triethylamine
pyr: pyridine
DMAP: dimethylaminopyridine Procedure for Isolating Compound (I) from a Mixture of (I) and (II)

In a first step under argon, 58 g of the mixture from (I) and (II) were weighed into a 1 l Schlenk flask, 450 ml of degassed o-xylene was added and the resulting mixture was stirred at 110° C. for 2 h. This dissolved the majority of the solid. The mixture was then brought to room temperature (RT) overnight with stirring. The accumulated solid was filtered off and dried.

Quantity of solid: 30 g corresponding to 52%.
Compound (I) content determined by $^{31}$P NMR: 139.2 (75.2%)
Compound (II) content determined by $^{31}$P NMR: 142.5 and 140.9 (20.0%) and additional hydrolysis and ligand decomposition products.

In a second step, 14.8 g of the solid from the first step were weighed into a 500 ml Schlenk flask under argon, 80 ml of degassed o-xylene were added and the resulting mixture was stirred at 100° C. for 1.5 h. This dissolved the majority of the solid. The mixture was then brought to room temperature overnight with stirring. The accumulated solid was filtered and dried.

Quantity of solid: 9.8 g corresponding to 66%.
Compound (I) content determined by $^{31}$P NMR: 139.2 (92.2%)
Compound (II) was no longer detectable. The remainder (7.8%) consisted merely of hydrolysis products or ligand decomposition products (such as oxides).

Should the product still comprise residual amounts of compound (II) after the second step, said second step may be repeated (=third step).

Analytical Verification of Compound (I)

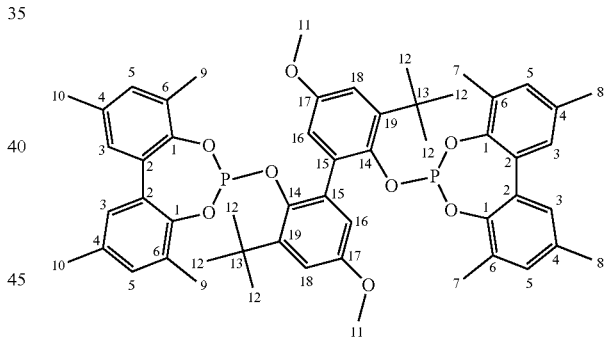

TABLE 1

Assignment of the signals to the atoms in 6,6'-((3,3'-di-tert-butyl-5,5'-dimethoxy-[1,1'-biphenyl]-2,2'-diyl)bis(oxy))bis(2,4,8,10-tetramethyldibenzo[d,f][1,3,2]dioxaphosphepine)

| Number | d $^1$H/ppm | d $^{13}$C/ppm |
|---|---|---|
| 1 | — | 145.4 |
| 2 | — | 133.5 |
| 3 | 7.01 | 128.0 |
| 4 | — | 130.0 |
| 5 | 6.88 | 130.9 |
| 6 | — | 146.1 |
| 7 \| 8 \| 9 \| 10 | 1.99 \| 2.28 \| 2.32 | 16.7 \| 16.9 \| 20.7 \| 20.8 |
| 11 | 3.77 | 55.5 |
| 12 | 1.14 | 29.9 |
| 13 | — | 35.2 |
| 14 | — | 145.4 |
| 15 | — | 130.5 |

TABLE 1-continued

Assignment of the signals to the atoms in 6,6'-((3,3'-di-tert-butyl-5,5'-dimethoxy-[1,1'-biphenyl]-2,2'-diyl)bis(oxy))bis(2,4,8,10-tetramethyldibenzo[d,f][1,3,2]dioxaphosphepine)

| Number | d $^1$H/ppm | d $^{13}$C/ppm |
|---|---|---|
| 16 | 6.83 | 113.5 |
| 17 | — | 154.8 |
| 18 | 6.93 | 115.1 |
| 19 | — | 143.2 |

The invention claimed is:

1. A process for preparing a compound of formula (I):

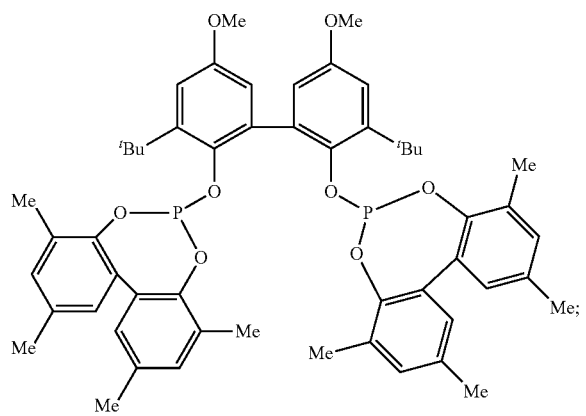

(I)

the process comprising:
- a) reacting 3,3',5,5'-tetramethyl-2,2'-dihydroxybiphenyl with $PCl_3$ in an inert gas atmosphere to obtain a phosphorochloridite derivative;
- b) reacting at least 2 equivalents of the phosphorochloridite derivative obtained in a) with 1 equivalent of 5,5'-dimethoxy-3,3'-di-tert-butyl-2,2'-dihydroxybiphenyl in an inert gas atmosphere to obtain a crude product;
- c) adding to the crude product from b) a solvent or a solvent mixture comprising at least one solvent selected from the group consisting of: o-xylene, toluene, methanol, ethanol, butanol and isopropanol to obtain a crude product mixture;
- d) heating the crude product mixture from c) to dissolve the crude product and obtain a solution;
- e) cooling down the solution from d) to precipitate the compound according to formula (I) from the solution; and
- f) filtering-off the precipitated compound according to formula (I).

2. The process according to claim 1 wherein process operations c) to f) are repeated.

3. The process according to claim 1, wherein the cooling down in e) comprises cooling the solution to room temperature.

4. The process according to claim 1, wherein the solvent in c) comprises o-xylene.

5. The process according to claim 1, wherein the mixture is heated to a temperature in the range of from 80° C. to 140° C. in d).

6. The process according to claim 1, wherein the reacting in b) is carried out in the presence of at least one base.

7. The process according to claim 6, wherein the base is an amine selected from the group consisting of triethylamine, dimethylaminopyridine, pyridine and tributylamine.

* * * * *